United States Patent [19]

Kuckert et al.

[11] Patent Number: 5,300,656
[45] Date of Patent: Apr. 5, 1994

[54] COUMARIN DERIVATIVES, PROCESS FOR THEIR PREPARATION, THEIR USE AND THIAZOLYL ACETIC ACID DERIVATIVES AS INTERMEDIATES

[75] Inventors: Eberhard Kuckert, West Haven, Conn.; Gunther Beck, Leverkusen, Fed. Rep. of Germany; Florin Seng, Bergisch Gladbach, Fed. Rep. of Germany; Antonius Löbberding, Wuppertal, Fed. Rep. of Germany

[73] Assignee: Bayer Aktiengesellschaft, Leverkusen, Fed. Rep. of Germany

[21] Appl. No.: 915,772

[22] Filed: Jul. 16, 1992

Related U.S. Application Data

[63] Continuation of Ser. No. 610,864, Nov. 8, 1990, abandoned.

[30] Foreign Application Priority Data

Nov. 21, 1989 [DE] Fed. Rep. of Germany ....... 3938598
Aug. 23, 1990 [DE] Fed. Rep. of Germany ....... 4026613

[51] Int. Cl.$^5$ ............... C07D 405/04; C07D 405/12; C07D 311/16; C07D 11/80
[52] U.S. Cl. ........................ 549/288; 544/151; 544/326; 548/159; 548/201
[58] Field of Search ............. 548/159, 201; 549/288; 544/236, 151

[56] References Cited

U.S. PATENT DOCUMENTS

| | | | |
|---|---|---|---|
| 4,404,389 | 9/1983 | Vamvakaris | 548/201 |
| 4,547,579 | 10/1985 | Möckli | 549/288 |
| 4,764,622 | 8/1988 | Claussen | 548/159 |

FOREIGN PATENT DOCUMENTS

| | | | |
|---|---|---|---|
| 0025136 | 3/1981 | European Pat. Off. | |
| 0032670 | 7/1981 | European Pat. Off. | |
| 0056577 | 7/1982 | European Pat. Off. | |
| 0101897 | 3/1984 | European Pat. Off. | |
| 2710285 | 9/1977 | Fed. Rep. of Germany | |
| 2712408 | 10/1977 | Fed. Rep. of Germany | |
| 154402 | 3/1982 | Fed. Rep. of Germany | 549/288 |
| 3609804 | 9/1987 | Fed. Rep. of Germany | 548/201 |

OTHER PUBLICATIONS

Chemical Abstracts, vol. 77, No. 6, Aug. 7, 1972, p. 107, No. 36362y.

Primary Examiner—Robert Gerstl
Attorney, Agent, or Firm—Sprung Horn Kramer & Woods

[57] ABSTRACT

Coumarin deviatives of the formula

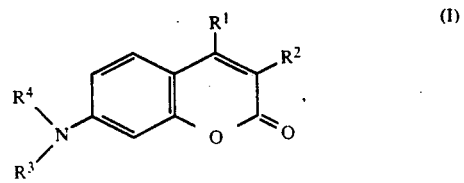

in which
$R^1$ denotes cyano,
$R^2$ represents phenyl or thiazolyl bonded in the 2-, 4-, or 5-position,
$R^3$ denotes hydrogen, $C_1$–$C_4$-alkyl or $C_1$–$C_4$-alkoxycarbonyl-$C_1$–$C_4$-alkyl and
$R^4$ represents hydrogen, $C_1$–$C_4$-alkyl or phenylsulphonyl, where $C_1$–$C_4$-alkyl can be substituted by hydroxyl, amino, carboxyl or $C_1$–$C_4$-alkoxy-carbonyl and phenyl can be monosubstituted or disubstituted by chlorine, bromine or $C_1$–$C_4$-alkyl, where furthermore $R^3$ and $R^4$, together with the N atom which they substitute, can denote a morpholine ring, a piperazine ring or a triazole ring which can carry one or two substituents from the group comprising methyl, ethyl and phenyl, and
where furthermore one of the radicals $R^2$, $R^3$ and $R^4$ denotes or carries a primary or secondary amino group, the hydroxyl group, the carboxyl group or the $C_1$–$C_4$-alkoxy-carbonyl group or can be converted into such a group by hydrolysis or hydrogenation, are suitable for dyeing biologically active compounds.

3 Claims, No Drawings

COUMARIN DERIVATIVES, PROCESS FOR THEIR PREPARATION, THEIR USE AND THIAZOLYL ACETIC ACID DERIVATIVES AS INTERMEDIATES

This application is a continuation of application Ser. No. 610,864, filed Nov. 8, 1990, now abandoned.

SUMMARY OF THE INVENTION

The invention relates to courmarin derivatives of the formula

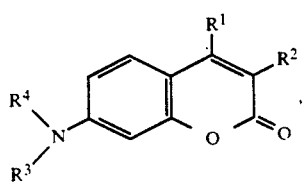

in which
  $R^1$ denotes hydrogen or cyano,
  $R^2$ denotes phenyl or thiazolyl bonded in the 2-, 4-or 5-position,
where phenyl is substituted by nitro, cyano, amino, $-CH-C_1-C_4$-alkyl, $-C_1-C_4$-alkyl$-NH_2$, $-C_1-C_4$-alkyl-NH$-C_1-C_4$-alkyl, carboxyl, $C_1-C_4$-alkoxy-carbonyl, $C_1-C_4$-alkylcarbonyloxy, hydroxyl, $C_1-C_4$-alkylamino-carbonyl or $C_1-C_4$-alkylcarbonyl-amino and can additionally be substituted by $C_1-C_4$-alkyl, fluorine, chloride or bromine, and where thiazolyl is monosubstituted or disubstituted by chlorine, cyano, carboxyl or $C_1-C_4$-alkoxy-carbonyl, where, in the case of distribution, the two substituents may be different and where the 4- and the 5-position can together carry a fused benzene ring which can be substituted by carboxyl, amino or hydroxyl,
  $R^3$ denotes hydrogen, $C_1-C_4$-alkyl or $C_1-C_4$-alkoxycarbonyl-$C_1-C_4$-alkyl and
  $R^4$ represents hydrogen, $C_1-C_4$-alkyl or phenylsulphonyl, where $C_1-C_4$-alkyl can be substituted by hydroxyl, amino, carboxyl or $C_1-C_4$-alkoxy-carbonyl and phenyl can be monosubstituted or disubstituted by chlorine, bromine or $C_1-C_4$-alkyl, where furthermore $R^3$ and $R^4$, together with the N atom which they substitute, can denote a morpholine ring, a piperazine ring or a triazole ring which can carry one or two substituents from the group comprising methyl, ethyl and phenyl, and
where furthermore one of the radicals $R_2$, $R_3$ and $R_4$ denotes or carries a primary or secondary amino group, the hydroxyl group, the carboxyl group or the $C_1-C_4$-alkoxy-carbonyl group or can be converted into such a group by hydrolysis or hydrogenation.

DETAILED DESCRIPTION OF THE INVENTION

The invention preferably relates to coumarin derivatives of the formula

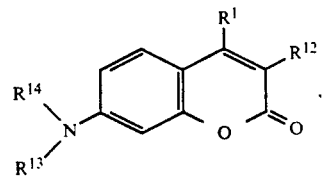

in which
  $R^1$ denotes hydrogen or cyano,
  $R^{12}$ represents phenyl or thiazolyl bonded in the 2-, 4-or 5-position, where phenyl can be substituted by carboxyl, $C_1-C_4$-alkyl-carbonyloxy, amino, $-N$-$H-C_1-C_4$-alkyl, $-C_1-C_4$-alkyl-$NH_2$, $C_1-C_4$-alkyl, cyano, fluorine, chlorine or bromine and where thiazolyl can be substituted by chlorine, cyano or carboxyl or a benzene ring fused in the 4- and 5-position, which in turn can carry carboxyl or amino,
  $R^{13}$ denotes hydrogen, methyl or ethyl and
  $R^{14}$ represents $-C_1-C_4$-alkyl-OH, $-C_1-C_4$-alkyl-$NH_2$ or $C_1-C_4$-alkyl-COOH.
where furthermore $R^{13}$ and $R^{14}$, together with the N atom which they substitute, can denote a morpholine ring, a piperazine ring or a triazolyl ring which can be substituted by methyl, phenyl or methyl and phenyl, and where furthermore one of the radicals $R^{12}$, $R^{13}$ and $R^{14}$ denotes or carries a primary or secondary amino group, the hydroxyl group, the carboxyl group or the $C_1-C_2$-alkoxy-carbonyl group.

The invention particularly preferably relates to coumarin derivatives of the formula

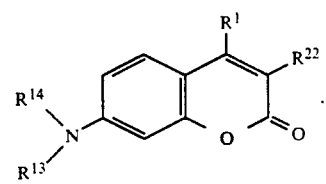

in which
  $R^1$, $R^{13}$ and $R^{14}$ have the abovementioned scope of meaning and
  $R^{22}$ represents phenyl or thiazolyl bonded in the 2-position, where phenyl can be substituted by para-carboxyl, para-amino, para-NH$-C_1-C_4$-alkyl, para-CH$_2$-NH$_2$, cyano, methyl or ethyl and where thiazolyl can be substituted by chlorine, cyano or carboxyl or a benzene ring fused in the 4- and 5-position which in turn can carry carboxyl or amino, where furthermore one of the radicals $R^{13}$, $R^{14}$ and $R^{22}$ denotes or carries a primary or secondary amino group, the hydroxyl group or the carboxyl group.

The invention furthermore relates to a process for the preparation of coumarin derivatives of the formula

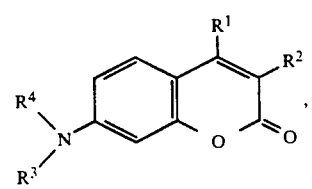

in which
- $R^1$ denotes hydrogen or cyano,
- $R^2$ represents phenyl or thiazolyl bonded in the 2-, 4-or 5-position, where phenyl is substituted by nitro, cyano, amino, —NH—$C_1$—$C_4$-alkyl, —$C_1$-$C_4$-alkyl-$NH_2$, —$C_1$-$C_4$-alkyl-NH—$C_1$-$C_4$-alkyl, carboxyl, $C_1$-$C_4$-alkoxycarbonyl, $C_1$-$C_4$-alkyl-carbonyloxy, hydroxyl, $C_1$-$C_4$-alkylamino-carbonyl or $C_1$-$C_4$-alkylcarbonyl-amino and can additionally be substituted by $C_1$-$C_4$-alkyl, fluorine, chlorine or bromine, and where thiazolyl is monosubstituted or disubstituted by chlorine, cyano, carboxyl or $C_1$-$C_4$-alkoxy-carbonyl, where, in the case of disubstitution, the two substituents may be different and where the 4- and the 5-position can together carry a fused benzene ring which can be substituted by carboxyl, amino or hydroxyl,
- $R^3$ denotes hydrogen, $C_1$-$C_4$-alkyl or $C_1$-$C_4$-alkoxycarbonyl -$C_1$-$C_4$-alkyl and
- $R^4$ represents hydrogen, $C_1$-$C_4$-alkyl or phenylsulphonyl, where $C_1$-$C_4$-alkyl can be substituted by hydroxyl, amino, carboxyl or $C_1$-$C_4$-alkoxy-carbonyl and phenyl can be monosubstituted or disubstituted by chlorine, bromine or $C_1$-$C_4$-alkyl, where furthermore $R^3$ and $R^4$, together with the N atom which they substitute, can denote a morpholine ring, a piperazine ring or a triazole ring which can carry one or two substituents from the group comprising methyl, ethyl and phenyl, and where furthermore one of the radicals $R^2$, $R^3$ and $R^4$ denotes or carries a primary or secondary amino group, the hydroxyl group, the carboxyl group or the $C_1$-$C_4$-alkoxy-carbonyl group or can be converted into such a group by hydrolysis or hydrogenation, which is characterized in that a) an m-aminophenol and a formylacetic acid derivative of the formulae

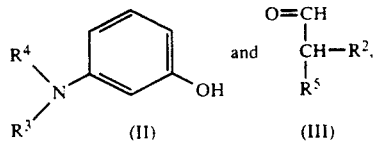

in which
$R^2$, $R^3$ and $R^4$ have the above scope of meaning and
$R^5$ denotes cyano, $C_1$-$C_4$-alkoxy-carbonyl or carboxyl, are reacted with one another or b) a salicylaldehyde and an acetic acid derivative of the formulae

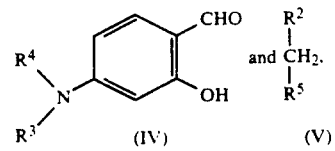

in which
$R^2$, $R^3$, $R^4$ and $R^5$ have the above scope of meaning, are reacted with one another, where if $R^5$=CN in a) and b), first an imino intermediate of the formula

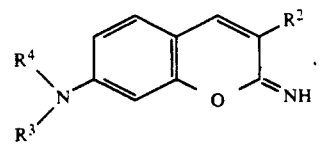

in which $R^2$, $R^3$, and $R^4$ have the above scope of meaning, is formed and this imino intermediate is hydrolysed with elimination of the imino group, or c) in the case in which $R^1$ denotes cyano, the imino intermediate as in b) or the coumarin derivative of the formula (I) is reacted with cyanide ions to give the imino-cyano intermediate or the cyano intermediate of the formulae

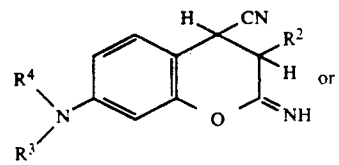

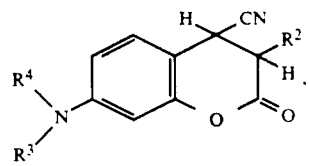

in which $R^2$, $R^3$ and $R^4$ have the above scope of meaning, and this is oxidized to the coumarin derivative and optionally additionally hydrolysed.

Some of the compounds of the formulae (V), namely the thiazolyl-acetic acid derivatives of the formula

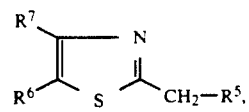

in which
- $R^6$ denotes chlorine or cyano and
- $R^7$ denotes chlorine or both substituents $R^6$ and $R^7$, together with the C atoms which they substitute, denote a benzene nucleau which can be substituted by carboxyl, amino or hydroxy and
- $R^5$ has the abovementioned scope of meaning, are new.

The invention therefore also relates to the intermediates of the formula (X).

The preparation of compounds of the formula (X) is described by way of example in the exemplary embodiments.

The coumarin derivatives according to the invention, in which one of the radicals $R^2$, $R^3$ and $R^4$ denotes or carries a primary or secondary amino group, the hydroxyl group, the carboxyl group or the $C_1$-$C_4$-alkoxycarbonyl group, are capable of binding to biologically active compounds via these mentioned groups and are therefore suitable for dyeing biologically active compounds. Such dyed biologically active compounds can be employed, for example, in immunoassay methods for the detection of complementary compounds thereof. In this procedure, the fluorescence property of the coumarin derivatives according to the invention used for dyeing is made use of. The biologically active compounds and complementary compounds thereof are, for example, the combination antigen/antibody or two complementary DNA strands. In order to avoid unpredictable multiple reactions between the coumarins and biologically active compounds, the coumarins according to the invention are restricted in that only one of the radicals $R^2$, $R^3$ and $R^4$ denotes or carries one of the said groups capable of binding.

The invention therefore also relates to the use of the coumarin derivatives of the formula (I) according to the invention for the dyeing of biologically active compounds.

$C_1$-$C_4$-Alkyl or $C_1$-$C_4$-alkoxy can be straight-chain or branched and are, for example, methyl, ethyl, propyl, isopropyl, butyl, isobutyl, methoxy, ethoxy, propoxy, isopropoxy, butoxy or isobutoxy. Preferentially, methyl, ethyl, methoxy and ethoxy may be mentioned. Preferred $C_1$-$C_4$-alkoxy-carbonyl is methoxy-carbonyl and ethoxycarbonyl.

The preparation of the coumarin derivatives according to the invention as in preparation variant b) in the sense of a Knoevenagel condensation may be exemplified, for example, by the following equation:

a treatment with dilute acids is carried out in the presence of relatively large amounts of alcohol (methanol, ethanol, propanol) at temperatures in the range °–45° C., the conversion of the imino intermediate being achieved with retention of the ester groups. If the free carboxyl groups are intended to be formed from ester groups originally present in the coumarin derivative, the reaction for the conversion of the imino intermediates can be carried out using more highly concentrated aqueous acids at higher temperatures, for example in the range 70°100° C., hydrolysis to the carboxyl group simultaneously taking place.

In the radicals $R^2$ and $R^3$, for example, a functional group required according to the invention can be generated from the range comprising the primary and secondary amino group, the hydroxyl group, the carboxyl group or the $C^1$-$C^4$-alkoxy-carbonyl group by further reactions. Thus, in the example of the above equation, the phenylsulphonyl group as the radical $R^4$ can be removed by hydrolysis, for example with 80% strength sulphuric acid, so that the radicals $R^3$ and $R^4$, together with the N atom which they substitute, form a primary amino group. Beforehand, however, likewise in the sense of the above equation, the said N atom can be selectively monoalkylated, for example with the aid of diethyl sulphate in the presence of weak alkalis; then

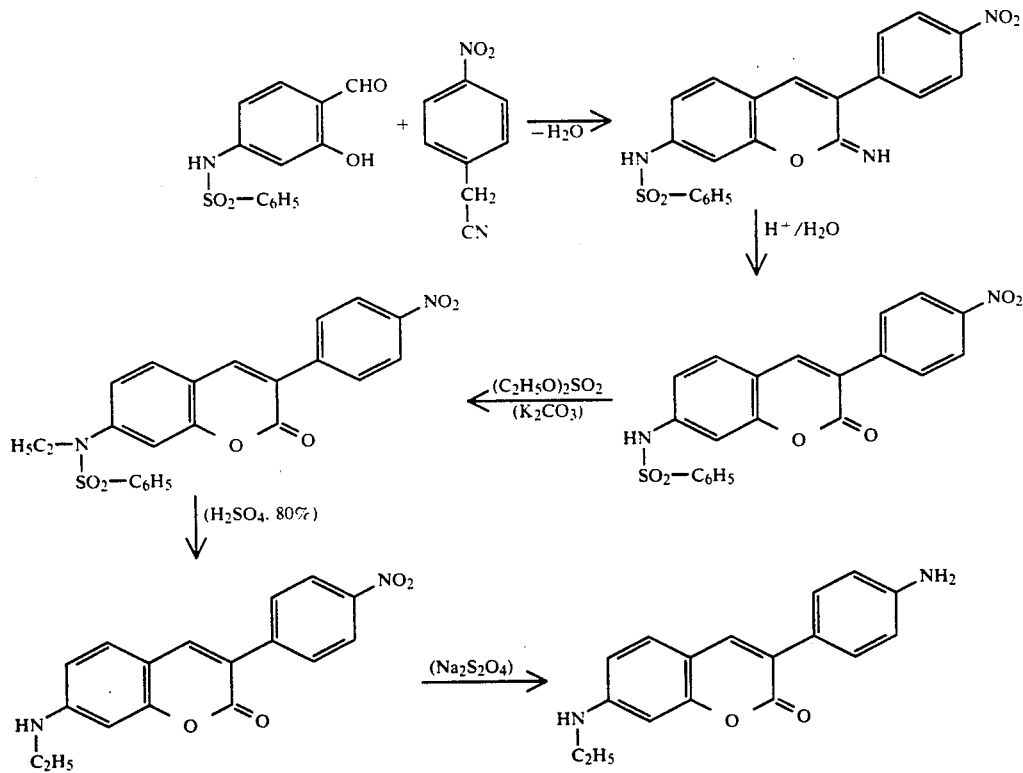

In this process, a salicylaldehyde which, corresponding to formula (IV), is substituted in the paraposition to the aldehyde group is condensed with an acetic acid derivative which is substituted corresponding to formula (V), with exclusion of water, where in the case in which the acetic acid derivative is acetonitrile, the imino intermediate, as shown in the above equation, is first formed, which can then be converted into the respective coumarin derivative by treatment with dilute acids, for example with dilute hydrochloric acid. If the desired coumarin derivative contains ester groups, such only the phenylsulphonyl group is hydrolytically removed, and $R^3$ and $R^4$, together with the N atom which they substitute, form a secondary amino group. Still furthermore, as likewise shown in the equation, the nitro group present within the radical $R^2$ can be reduced to the primary amino group; for this purpose, for example, sodium dithionite can be employed as a reducing agent.

As free primary amino groups react with salicylaldehydes to give Schiff's bases, it is necessary to protect those primary amino groups, for example by an acyl group or the phenylsulphonyl group. Such a protecting group can be removed again by hydrolysis in the manner already described above. Of course, in the sense of the above embodiments a free primary amino group can also be generated from a nitro group or a cyano group by reduction (hydrogenation). Suitable reducing agents are sodium dithionite, tin(II) salts or catalytically activated hydrogen.

In the case of the introduction and hydrogenation of a cyano group, the following reaction course results:

The reaction according to a) can be represented in terms of formulae, for example, by the following equation:

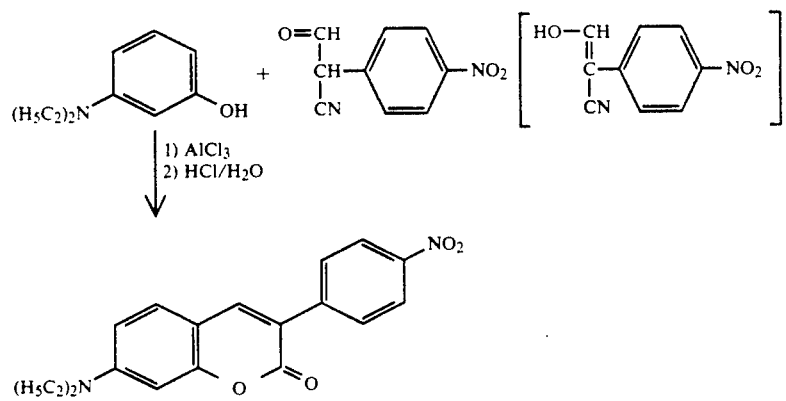

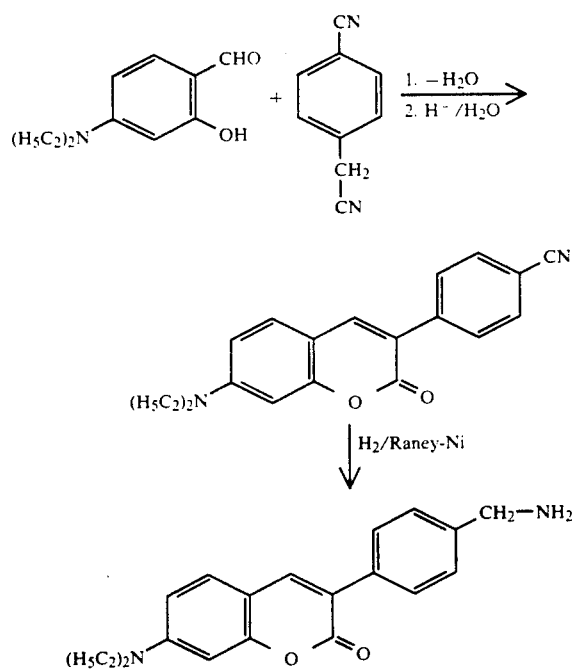

In accordance with a further preparation, an aminophenol of the formula (II) and a formylacetic acid derivative of the formula (III) can be used according to a). These two starting materials are condensed in a similar manner, as has been described further above for b), with the exclusion of water. In the case in which $R^5$ denotes methoxycarbony or ethoxycarbonyl, methanol or ethanol is additionally removed. In the case in which $R^5$ denotes cyano, the imino intermediate of the formula (VI) is formed first as in the reaction sequence according to b), and is then converted into the coumarin derivative using dilute acid.

The functionalities which are displayed by the coumarin derivatives according to the invention, namely primary or secondary amino groups, hydroxyl groups, carboxyl groups or $C_1$-$C_4$-alkoxycarbonyl groups or the said groups from which those functional groups can be generated (nitro group, cyano group or amino groups protected by acyl or phenylsulphonyl) can be introduced either via the salicylaldehydes employed for the preparation or the aminophenols employed or via the said acetic acid derivatives in the context of the preparation possibilities described. In the former case, these groups are functional groups located in the 7-position of the coumarin derivative; in the latter case they are functional groups introduced in the 3-position of the coumarin derivatives.

The coumarin derivatives according to the invention can furthermore be provided with a cyano group in the 4-position by reaction with cyanide ions and subsequent oxidation. This results in a bathochromic shift of the wavelength of the light absorption of such coumarin derivatives. This reaction can be carried out both on the coumarin derivatives of the formula (I) in which $R^1$ denotes hydrogen and on the imino intermediate of the formula (VI). The reaction is carried out in a solvent suitable for the coumarin derivative or imino intermediate, for example dimethylformamide. The cyanide ions are added, for example, in the form of an aqueous sodium cyanide or potassium cyanide solution. The following oxidation can be carried out, for example, using lead tetraacetate, hydrogen peroxide, bromine, persulphates or other oxidizing agents known to the person skilled in the art.

The introduction of the cyano group according to c) can be represented in terms of formulae, for example, as follows:

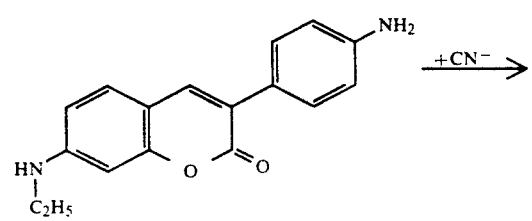

-continued

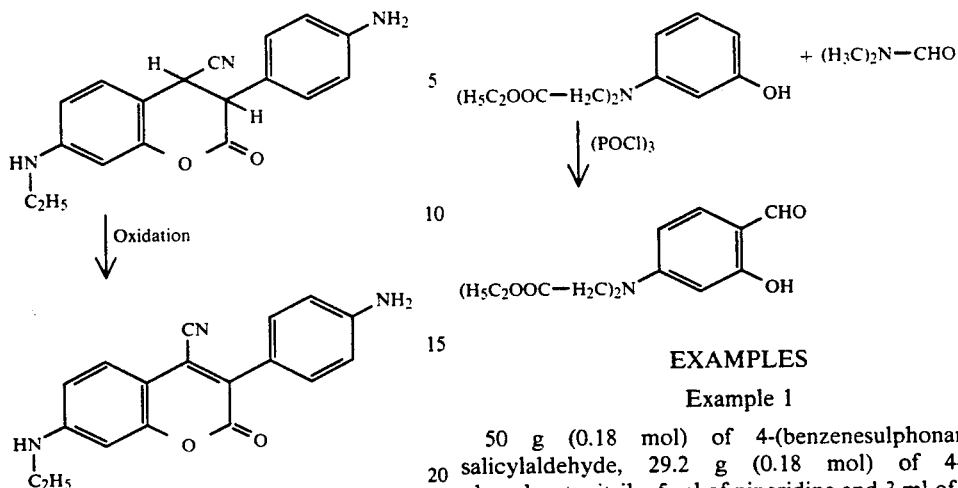

↓ Oxidation

In the case of coumarins containing carboxyl groups, the reaction with cyanide ions can be carried out in the form of their sodium salts, which is sufficiently soluble, for example, in dimethylformamide.

The aminophenols required for the preparation variant a) can be obtained by reaction of resorcinol with a primary or secondary amine with elimination of water, as is shown by way of example by the following equation.

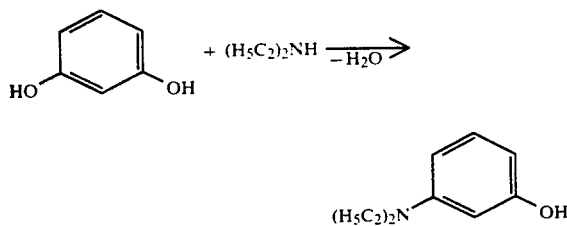

However, such m-aminophenols can also be obtained by selective N-alkylation of m-aminophenols with alkyl halides in the presence of an acid-binding agent, for example calcium carbonate, in a fundamentally known manner, as is shown by way of example by the following equation:

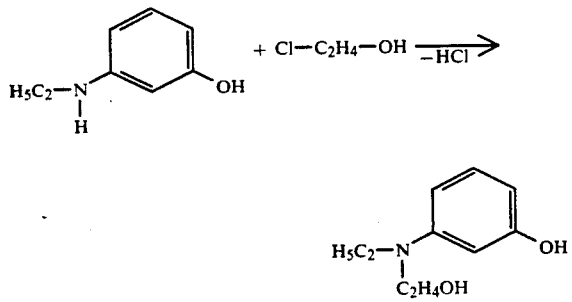

The salicylaldehydes required for the preparation variant b) can be obtained from the basic m-aminophenols, phosphorus oxychloride and a formamide, for example, dimethylformamide, by Vilsmeyer reaction, as is shown by way of example by the following equation:

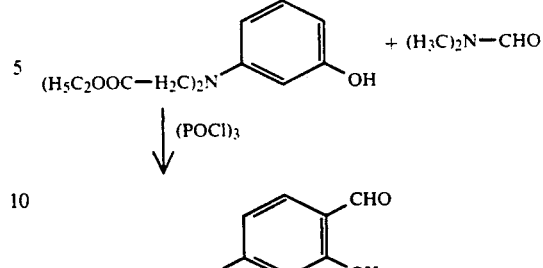

EXAMPLES

Example 1

50 g (0.18 mol) of 4-(benzenesulphonamide)-salicylaldehyde, 29.2 g (0.18 mol) of 4-nitrophenylacetonitrile, 5 ml of piperidine and 3 ml of acetic acid were heated under reflux for three hours in 400 ml of ethanol. After cooling, the precipitated intermediate was filtered off with suction and heated with 200 ml of half-concentrated hydrochloric acid for 1 hour. After neutralizing with sodium hydroxide solution, 66.5 g of 7-benzenesulphonamido-4-(4-nitrophenyl)-coumarin precipitated. (86%)

Example 2

30 g (0.07 mol) of 7-benzenesulphonamido-3-(4-nitrophenyl)-coumarin, 30 g (0.21 mol) of finely ground potassium carbonate and 32.4 g (0.21 mol) of diethyl sulphate were heated to 50° C. with good stirring for 48 h in 200 ml of dimethylformamide (DMF). After distilling off the dimethylformamide, the residue was thoroughly stirred with water. Yield of 7-(N-ethyl-N-benzenesulphonylamino)-3-(4-nitrophenyl)-coumarin 30.3 g (88%) melting point: 165° C.

Example 3:

30 g (0.067 mol) of 7-(N-ethyl-N-benzylsulphonamido-3-(4-nitrophenyl)-coumarin were heated to 100° C. for 3 hours in 30 ml of 80% strength sulphuric acid. The reaction mixture was added to 50 ml of water with ice-cooling and neutralized using sodium hydroxide solution. The product was filtered off with suction and washed with water.

Yield of 7-ethylamino-3-(4-nitrophenyl)-coumarin: 11 g (50%) melting point: 230° C.

Example 4

10 g (0.032 mol) of 7-ethylamino-3-(4-nitrophenyl)-coumarin were heated to 100° C. in 70 ml of DMF, and a suspension of 20 g (0.11 mol) of sodium dithionite in 50 ml of water was added dropwise with good stirring. After 25 min, the solvent was distilled off and the residue was thoroughly stirred with 100 ml of water. After filtering off with suction, this residue was heated under reflux for 2 hours with 40 ml of concentrated hydrochloric acid and 80 ml of ethanol to destroy sulphamic acids formed. The mixture was neutralized using sodium hydrogen carbonate and the precipitate was filtered off with suction.

Yield of 7-ethylamino-3-(4-aminophenyl)-coumarin: 8.1 g (91%) melting point: 263° C.

Example 5

In the same way as in Examples 1–4, but using dimethyl sulphate instead of diethyl sulphate (compare Example 2), 7-methylamino-3-(4-aminophenyl)-coumarin was obtained.

Example 6

13.6 g (0.07 mol) of 4-diethylamino-salicylaldehyde were heated under reflux with 10 g (0.07 mol) of α-cyanotoluonitrile, 5 ml of piperidine and 3 ml of acetic acid in 200 ml of ethanol. After cooling, the mixture was filtered off with suction and the residue was heated to reflux for 1 hour with 100 ml of half-conc. hydrochloric acid. After neutralizing with sodium hydroxide solution, the product was washed with water and filtered off with suction.

Yield of 7-diethylamino-3-(4-cyanophenyl)-coumarin 15.7 g (70%)

Example 7

15 g (0.047 mol) of 7-diethylamino-3-(4-cyanophenyl)-coumarin were hydrogenated at 100 bar hydrogen pressure and 70° C. in 100 ml of ethanol and 30 ml of liquid ammonia using Raney nickel as a catalyst. After completion of the reaction, the solvent was distilled off in a rotary evaporator, and the residue was boiled with DMF and filtered. After distilling off the DMF, the residue was dissolved in toluene with the addition of Tonsil and allowed to crystallize. 4.9 g of 7-diethylamino-3-(4-methylaminophenyl)-coumarin precipitated at 0° C. (32%), melting point: 118° C.

Example 8

20.7 g (0.1 mol) of 4-morpholino-salicylaldehyde, 16.2 g (0.1 mol) of p-nitrophenyl-acetonitrile, 1.7 ml of piperidine and 1 ml of acetic acid were heated to reflux for 3 hours in 250 ml of ethanol. An additional 50 ml of conc. hydrochloric acid were then added and the mixture was heated for a further 2 hours. After cooling the mixture, it was neutralized using sodium hydroxide solution, and the product was filtered off with suction and washed with water.

Yield of 7-morpholino-3-(4-nitrophenyl)-coumarin: 26.0 g (74%), melting point: >250° C.

Example 9

5 g (0.014 mol) of 7-morpholino-3-(4-nitrophenyl)-coumarin were heated to 60° C. in 20 ml of DMF, and a suspension of 10 g (0.055 mol) of sodium dithionite in 20 ml of water was added dropwise. After 1 hour, the solvent was distilled off in vacuo and the residue was boiled for 2 hours with a mixture of 20 ml of ethanol and 30 ml of concentrated hydrochloric acid. After neutralization with sodium hydroxide solution, the precipitated product was filtered off with suction, dried at 50° C. and then recrystallized from boiling chlorobenzene with the addition of Tonsil.

Yield of 7-morpholino-3-(4-aminophenyl)-coumarin: 2.6 g (57%), melting point: 211°–216° C.

Example 10

In the same way as in Examples 8 and 9, but using 4-(2-[4'-methyl-5'-phenyl-dihydro-1,2,3-triazinyl])-salicylaldehyde instead of 4-morpholino-salicylaldehyde, 7-(2-[4'-methyl-5'-phenyl-dihydro-1,2,3-triazinyl])-3-(4-aminophenyl)-coumarin was obtained in 63% of the theoretical yield, melting point: >250° C.

Example 11

7-(N-Ethyl-N-β-hydroxyethylamino)-3-(4-nitrophenyl)-coumarin was obtained in 80% of the theoretical yield from 4-(N-ethyl-N-β-hydroxyethylamino)-salicylaldehyde and p-nitrophenyl-acetonitrile analogously to Example 8 and 7-(N-ethyl-N-β-hydroxyethylamino)-3-(4'-aminophenyl)-coumarin was further obtained from this analogously to Example 9 in 45% of the theoretical yield, melting point 155° C.

Example 12

10.8 g (0.05 mol) of methyl 4-chloro-5-cyanothiazolyl-2-acetate, 10.46 g (0.05 mol) of 4-(N-2-hydroxyethyl-N-ethyl-amino)-salicylaldehyde, 0.5 ml of piperidine and 0.3 ml of acetic acid were heated under reflux for 4 hours in 150 ml of ethanol. The product precipitated on cooling was recrystallized from boiling chlorobenzene with the addition of bleaching earth (Tonsil). 10.0 g (53%) of 7-(N-ethyl-N-β-hydroxyethylamino)-3-(4'-chloro-5'-cyano-thiazol-2'-yl)-coumarin of melting point 226° C. were obtained.

Example 13

Analogously to Example 12 using ethyl 4,5-dichlorothiazolyl-2-acetate, 7-(N-ethyl-N-β-hydroxyethylamino)-3-(4',5'-dichloro-thiazol-2'-yl)-coumarin of melting point 230° C. was obtained in 48% of the theoretical yield.

Examole 14

Analogously to Example 12 using methyl 4,5-benzothiazolyl-2-acetate, 7-(N-ethyl-N-β-hydroxyethylamino)-3-(4',5'-benzothiazol-2'-yl)-coumarin of melting point 221° C. was obtained in 63% of the theoretical yield.

Example 15

By addition of cyanide and subsequent oxidation, 7-(N-ethyl-N-β-hydroxyethylamino)-3-(4'-chloro-5'-cyanothiazol-2'-yl)-4-cyano-coumarin of melting point 292° C. was obtained from the coumarin of Example 12 in 64% of the theoretical yield.

Example 16

Analogously to Example 15, 7-(N-ethyl-N-β-hydroxyethylamino)-3-(4',5'-benzothiazol-2'-yl)-4-cyanocoumarin of melting point 263° C. was obtained from the coumarin of Example 14 in 26% of the theoretical yield.

Examole 17

27.7 g (0.1 mol) of BESA (4-(benzenesulphonamido)-salicylaldehyde), 17.5 g (0.1 mol) of methyl 4-cyanomethyl-benzoate, 2.5 ml of piperidine and 1.7 ml of glacial acetic acid were heated under reflux for 3 hours in 200 ml of ethanol. After cooling, the mixture was filtered off with suction and the precipitated material was heated under reflux for 2 hours with 100 ml of methanol and 100 ml of conc. hydrochloric acid. 25.3 g (58%) of 7-benzenesulphonamido-3-(4,-methylcarboxyphenyl)-coumarin precipitated, which could be used without further prepurification for Example 18.

Example 18

35 g (0.08 mol) of the compound from Example 17, 30 g (0.22 mol) of potassium carbonate, 30.8 g (0.2 mol) of diethylsulphate and 200 ml of DMF were heated to 50°

C. with good stirring for 48 h. The solvent was then distilled off and the residue was thoroughly stirred with water. After filtering off with suction and drying, 35 g of 7-(N-ethyl-N-benzenesulphonylamino)-3-(4'-methylcarboxyphenyl)-coumarin (83%) were obtained.

Example 19

35 g (0.075 mol) of 7-(N-ethyl-N-benzenesulphonylamino) -3-(4'-methylcarboxyphenyl)- courmin were heated to 100° C. for 3 hours in 65 ml of 80% strength sulphuric acid. For working-up, the mixture was cautiously added to 400 ml of ice-water and brought to pH 6.5 using sodium hydroxide solution. After filtering off with suction, the precipitate was washed with water.

Yield: 16 g (68%) of 7-(N-ethyl)-3-(4'-carboxyphenyl)coumarin.

Example 20

Analogously to Example 13 using 4-(N,N-bis[ethoxycarbonylmethyl]-amino)-salicylaldehyde. 7-(N'N-bis-[ethoxycarbonylmethyl]-amino)-3-(4,,5,-dichlorothiazol-2'-yl)-coumarin of melting point 190° C. was obtained in 62% of the theoretical yield.

Example 21

A solution of 1 g (0.015 mol) of potassium cyanide in 10 ml of water was added at 40° C. to 3.5 g (0.0072 mol) of the coumarin from Example 20 in 50 ml of DMF and the mixture was stirred at this temperature for three hours. It was cooled to 0°-5° C. and 4.0 g (0.009 mol) of lead tetraacetate in 10 ml of DMF were added. After 2 hours, the precipitated material was filtered off with suction, washed with methanol and recrystallized from 200 ml of boiling toluene with the addition of bleaching earth (Tonsil). Yield: 1.6 g (43%) of 7-(N,N-bis-[ethoxycarbonylmethyl]-amino)-3-(4',5'-dichlorothiazol of melting point 185° C.

Example 22

5.4 g (0.02 mol) of 4,5-bis(ethoxycarbonyl)-2-thiazolyl-acetonitrile, 4.2 g (0.02 mol) of 4-morpholinosalicylaldehyde, 0.5 ml of piperidine and 0.3 ml of acetic acid were heated under reflux for 3 hours in 100 ml of ethanol. The intermediate (imine) precipitated after cooling was stirred at 45° C. for 4 hours in 80 ml of ethanol, 10 ml of concentrated hydrochloric acid and 10 ml of water. After neutralization with 20% strength sodium hydroxide solution, the product was recrystalized from toluene with the addition of bleaching earth (Tonsil).

7.4 g (80%) of 7-(N-morpholino)-3-(4',5'-bis-[ethoxycarbonyl]-thiazol-2'-yl)-coumarin of melting point 265° C. were obtained.

Examole 23

5.6 g (0.02 mol) of 4-[N-ethyl-N-(4-ethylbutyrate)-amino]-salicylaldehyde, 3.5 g of benzothiazolylacetonitrile, 0.5 ml of piperidine and 0.3 ml of acetic acid were heated under reflux in 100 ml of ethanol for 3 hours. After distilling off the ethanol, the mixture was heated to boiling with 100 ml of half-concentrated hydrochloric acid for a further 2 hours. After cooling, it was adjusted to pH 6.5 with sodium hydroxide solution, and the precipitate was filtered off with suction and recrystallized from boiling acetic acid with the addition of active carbon. 5.5 g of 7-(N-ethyl-N-carboxy-tetramethyleneamino)-3-(4',5'-benzothiazol-2,-yl)-coumarin of melting point 218° C. were obtained in 67% of the theoretical yield.

Example 24

The compound

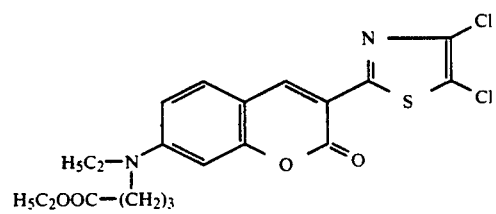

of melting point 137° C. in 50% of the theoretical yield was obtained analogously to the procedure described.

Example 25

The compound

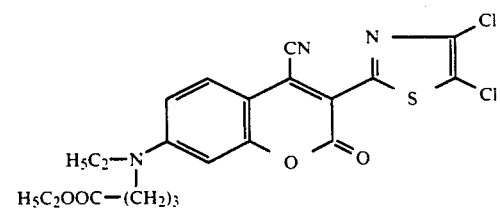

was obtained analogously to the procedure described.

Example 26

The compound

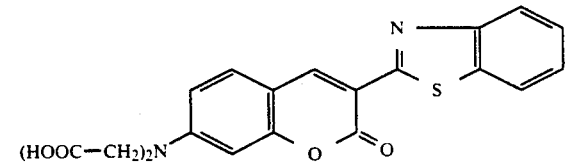

of melting point >300° C. in 32% of the theoretical yield was obtained analogously to the procedure described.

Example 27

The compound

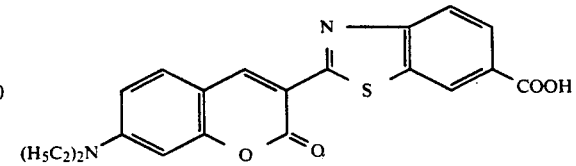

was obtained analogously to the procedure described.

Example 28

The compound

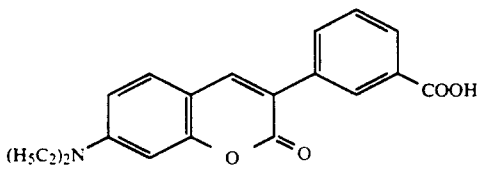

of melting point >300° C. in 67% of the theoretical yield was obtained analogously to the procedure described.

Examples 29–37

Synthesis of the m-aminophenols used

The m-aminophenols used could be obtained by two processes:
a) Reaction of resorcinol with a primary or secondary amine with elimination of water, as described in DE-OS (German Published Specification) 1,543,368.
b) Selective N-alkylation of m-aminophenols with alkyl halides in the presence of an acid-binding agent (for example calcium carbonate). Alkylating agent and acid-binding agent were preferably employed in 20–50% excess. N-alkylation took place selectively in this case.

Example 29

110 g (1.0 mol) of resorcinol, 89 g (1.0 mol) of N-(2-hydroxyethyl)-ethylamine and 6.2 g (0.1 mol) of boric acid were heated to 180°–200° C. and the water formed was distilled off over a period of about 8 hours. After cooling to 60° C., 130 ml of methanol were added and the methyl borate formed was distilled off. First unreacted amine and resorcinol, and subsequently the product were then distilled off in a high vacuum.

Boiling point: 191° C. (3 mbar) yield of 3-(N-2-hydroxyethyl-N-ethyl)aminophenol: 40%

Purity according to GC: 80%

This compound could also be prepared from N-ethyl-m-aminophenol and 2-chloroethanol by method b).

Example 30

149.1 g (1.0 mol) of 3-ethylaminophenol (92% purity), 120 g (1.2 mol) of calcium carbonate (ground) and 500 ml of DMF were heated to 120° C., and 80.5 g (1.0 mol) of 2-chloroethanol were slowly added dropwise in the course of 4–5 hours. The mixture was subsequently stirred at 125° C. for 12 h and the solvent was then distilled off. 300–500 ml of water were added to the residue and the mixture was filtered. After extracting by shaking with chloroform three times (150 ml each), the combined organic phases were distilled off. 67 g of product were obtained (purity 95%).

M.p.: (0.15) mbar: 180° C.

In order to protect the alcoholic OH group in the subsequent Vilsmeyer reaction, an acetylation was carried out as follows:

95 g (0.5 mol) of 3-(N-2-hydroxyethyl-N-ethyl)-aminophenol, 113 g (1.1 mol) of acetic anhydride and 87 g (1.0 mol) of pyridine were heated under reflux for 3 hours. For working-up, the mixture was added to 300 g of ice, rendered neutral with sodium hydrogen carbonate and extracted by shaking several times with chloroform. After drying over sodium sulphate, the combined organic phases were distilled in vacuo. 78.2 g (56%) of 3-(N-acetoxy-ethyl-N-ethyl)amino-acetoxyphenol passed over at 0.3 mbar and 166°–170° C.

Example 31

14.9 g (0.1 mol) of 3-ethylaminophenol (92% purity) were heated to 65° C. with 11 g (0.11 mol) of finely ground calcium carbonate in 35–50 ml of DMF. 16.7 g (0.1 mol) of ethyl bromoacetate were added dropwise in the course of 30 min. The mixture was subsequently stirred at 80° C. for 1 hour. After evaporating off the solvent, 100 ml of water and 50 ml of chloroform were added to the residue and the mixture was filtered. The aqueous phase was extracted again with chloroform. The combined organic phases were dried over sodium sulphate and then distilled in vacuo.

16.3 g (73%) of product passed over at 0.15 mbar and 167°–171° C.

The following (Examples 32–37) were prepared in an analogous manner

| Structure | Description |
|---|---|
| OH-C6H4-N(C2H5)(CH2-COO-C2H5) | from N-ethyl-m-aminophenol and ethyl bromoacetate according to method b). b.p. 167–171° C./0.15 mbar, 73% of the theoretical yield (Example 32) |
| OH-C6H4-N(CH3)(C2H4OH) | from resorcinol and N-β-hydroxy-ethyl-methyl-amine according to method a) in 63% of the theoretical yield. b.p. 170° C./0.4 mbar (Example 33) |
| OH-C6H4-N(piperazine)-C2H4OH | from resorcinol and N-β-hydroxy-ethyl-piperazine according to method a) in 40% of the theoretical yield. melting point 124–126° C. (Example 34) |
| OH-C6H4-N(CH2-COOC2H5)2 | from m-aminophenol according to method b) and ethyl bromoacetate in 40% of the theoretical yield, melting point 58° C., b.p. 180° C./0.2 mbar (Example 35) |
| OH-C6H4-N(C2H5)((CH2)3OH) | from N-ethyl-aminophenol and 3-bromo-n-propanol according to method b) in 36% of the theoretical yield, oil at room temperature (Example 36) |
| OH-C6H4-N(C2H5)((CH2)3-COOC2H5) | from N-ethyl-aminophenol and ethyl 3-bromo-n-butyrate according to method b) in 62% of the theoretical yield, b.p. 170° C./0.1 mbar (Example 37) |

Examples 38–43

Synthesis of the 4-amino-salicylaldehydes used by Vilsmeyer reaction from the basic 3-aminophenols. Hydroxyl groups were protected by acetylation and carboxyl groups by esterification.

Example 38

16.9 g (0.06 mol) of 3-(ethyl-N,N'-diacetate)aminophenol were dissolved in 40 ml of DMF and 12 g (7.4 ml, 0.078 mol) of phosphorus oxychloride were slowly added dropwise so that the internal temperature did not exceed 20° C. For working-up, the mixture was added to ice, neutralized with sodium hydroxide solution and extracted by shaking with chloroform. After drying, the combined organic phases, the chloroform was distilled off. The residue was boiled with toluene and Tonsil. Evaporation of the solvent yielded 12.6 g (68%) of product of melting point 70° C.

Example 39

12.34 g (7.8 ml, 0.08 mol) of phosphorus oxychloride were added dropwise to 18 g (0.068 mol) of 3-(N2-acetoxyethyl-N-ethyl-amino)-acetoxyphenol in 20 ml of DMF so that the internal temperature did not exceed 20° C. After 1 hour at this temperature, the mixture was heated to 60° C. for 5 h. For working-up, it was cautiously added to 200 g of ice, neutralized with sodium hydroxide solution and extracted by shaking several times with chloroform. After drying the combined organic phases, the chloroform was removed on a rotary evaporator and the remaining oil was stirred with half-concentrated hydrochloric acid for 6 hours to remove protecting groups. After neutralization, extraction by shaking with chloroform and drying and evaporation of the solvent, the residue was boiled with toluene and Tonsil. After filtration and removal of the toluene, 7.1 g (50%) of 4-(N-2-hydroxyethyl-N-ethyl-amino)-salicylaldehyde of melting point 60° C. remained.

The following (Examples 40–43) were prepared in an analogous manner

| Structure | Conditions |
|---|---|
| 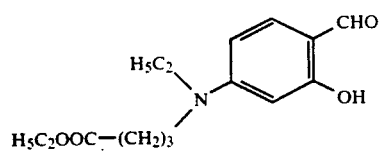 | at 100° C. reaction temperature in 48% of the theoretical yield, oil at room temperature (Example 40). |
| 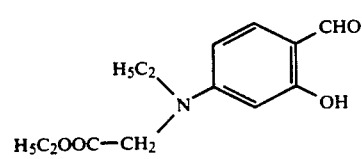 | at 100° C. reaction temperature in 56% of the theoretical yield, melting point 54° C. (Example 41). |
| 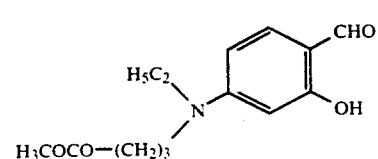 | at 100° C. reaction temperature in 30% of the theoretical yield, oil at room temperature (Example 42). |
| 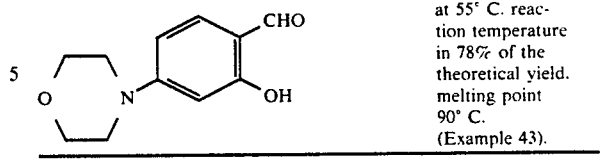 | at 55° C. reaction temperature in 78% of the theoretical yield, melting point 90° C. (Example 43). |

Example 44

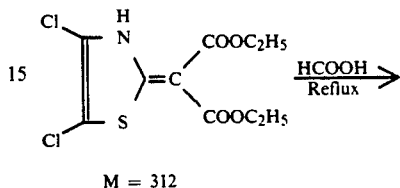

M = 312

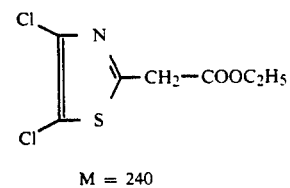

M = 240

656 g (2.1 mol) of diethyl 4,5-dichloro-2-thiazolylmalonate and 3 litres of pure formic acid were stirred under reflux for 7 hours. After evaporating in a rotary evaporator (509 g; quantitative), the residue was distilled with an oil pump. Yield 463 g (92% of theory) of ethyl 4,5-dichloro-2-thiazolylacetate. Boiling point 120° C./0.1 mbar. Melting point under 50° C. (recrystallizable from a little petroleum ether).

The following was obtained analogously:

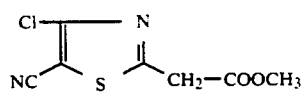

Methyl 4-chloro-5-cyano-2-thiazolylacetate. Melting point 63° C.

Example 45

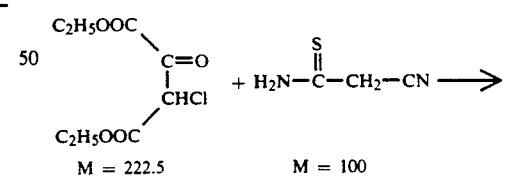

M = 222.5     M = 100

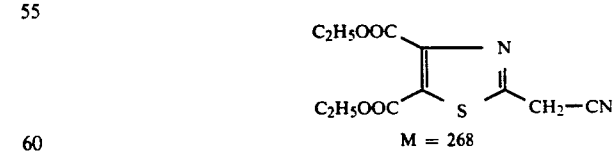

M = 268

40 g (0.4 mol) of cyanoacetic acid thioamide were dissolved in 200 ml of dimethylformamide. After addition of 111 g (0.5 mol) of diethyl chloroxalate, the mixture was stirred at room temperature for 4 days. It was then added to about 2.5 litres of ice-water, taken up with dichloromethane and the dichloromethane phase was concentrated. Fractional distillation in the range 150°-230° C./1.5-2 mbar yielded 11.6 g of crude product which was recrystallized from hexane-toluene (3:1). Yield: 7.6 g of 4,5-bis(ethoxycarbonyl)-2-thiazolylacetonitrile of a GC purity of 99.4%. Melting point 75.7-77° C.:

Example 46

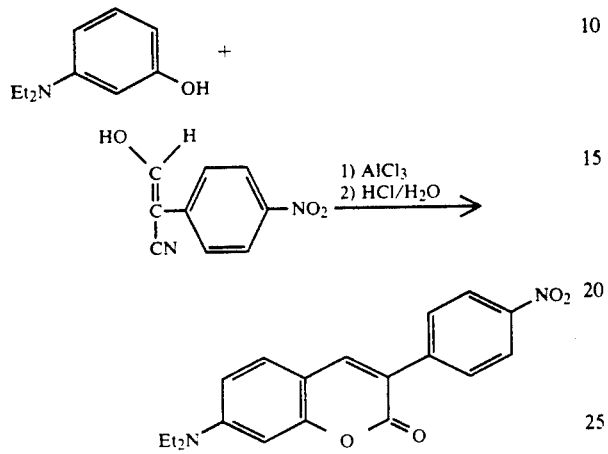

14.66 g (0.11 mol) of anhydrous aluminum chloride were initially introduced into 100 ml of nitrobenzene. 16.5 g (0.1 mol) of 3-N,N-diethylamino-phenol and 19 g (0.1 mol) of α-(hydroxymethylene)-4-nitrophenylacetonitrile (Preparation: B. Boose et. al., Bull. Soc. Chim. Belg., 1988, [97], 267-70) were added to this. The mixture was stirred at 100° C. for 2 hours, during which a precipitate deposited. The temperature was then increased to 130° C. and the mixture was stirred for a further 1.5 hours. After cooling to about 80° C., 100 ml of isopropanol and 50 ml of water were added. 30 ml of 37% strength hydrochloric acid were then added dropwise at 80°. After cooling and filtering off the resulting precipitate with suction, 29 g (85.8% of theory) of 3-(4-nitrophenyl)-7-diethylamino-coumarin were obtained as yellow crystals which melt at 162°3° C. after dissolving and allowing to crystallize from acetonitrile.

TABLE

Spectroscopic data (in nm) of the maximum excitation wavelength (Exc.$_{max}$), the maximum emission (Em.$_{max}$) and their difference (Δ Stokes) in the solvents (S) used and the fluorescence quantum yield FQ of the coumarin derivatives prepared in the examples given

| Example No. | Exc.$_{max}$ | Em.$_{max}$ | Δ Stokes | S | FQ |
|---|---|---|---|---|---|
| 4 | 399 | 533 | 134 | DMF | 0.77 |
| 5 | 400 | 529 | 129 | DMF | 0.76 |
| 7 | 403 | 484 | 81 | DMF | 0.72 |
| 7 | 401 | 503 | 102 | CH$_2$Cl$_2$ | 0.69 |
| 9 | 393 | 520 | 127 | DMF | 0.79 |
| 9 | 382 | 512 | 130 | CH$_2$Cl$_2$ | 0.74 |
| 10 | 378 | 512 | 134 | CH$_2$Cl$_2$ | 0.72 |
| 11 | 407 | 520 | 113 | DMF | 0.76 |
| 12 | 487 | 539 | 52 | DMF | 0.52 |
| 12 | 479 | 514 | 35 | CH$_2$Cl$_2$ | 0.79 |
| 13 | 472 | 518 | 46 | DMF | 0.63 |
| 13 | 456 | 500 | 44 | CH$_2$Cl$_2$ | 0.89 |
| 14 | 462 | 513 | 51 | DMF | 0.82 |
| 14 | 443 | 495 | 52 | CH$_2$Cl$_2$ | 0.85 |
| 15 | 568 | 641 | 73 | DMF | 0.11 |
| 16 | 530 | 629 | 99 | DMF | 0.34 |
| 16 | 522 | 595 | 73 | CH$_2$Cl$_2$ | 0.80 |
| 20 | 444 | 499 | 55 | DMF | 0.76 |
| 20 | 428 | 500 | 72 | CH$_2$Cl$_2$ | 0.88 |
| 21 | 505 | 600 | 95 | DMF | 0.65 |
| 21 | 483 | 557 | 74 | CH$_2$Cl$_2$ | 0.88 |
| 22 | 457 | 532 | 75 | DMF | 0.71 |
| 23 | 459 | 510 | 51 | DMF | 0.74 |
| 23 | 466 | 520 | 54 | H$_2$O | 0.31 |
| 24 | 467 | 515 | 48 | DMF | 0.50 |
| 24 | 465 | 501 | 36 | CH$_2$Cl$_2$ | 0.82 |
| 25 | 539 | 613 | 74 | DMF | 0.43 |
| 26 | 448 | 503 | 55 | DMF | 0.62 |
| 26 | 450 | 516 | 66 | H$_2$O | 0.83 |
| 27 | 476 | 520 | 44 | DMF | 0.74 |
| 27 | 473 | 504 | 31 | CH$_2$Cl$_2$ | 0.89 |
| 28 | 449 | 522 | 73 | DMF | 0.82 |
| 28 | 438 | 500 | 62 | CH$_2$Cl$_2$ | 0.89 |
| 29 | 440 | 506 | 66 | DMF | 0.84 |
| 30 | 404 | 484 | 80 | DMF | 0.76 |

What is claimed is:

1. A coumarin derivative of the formula

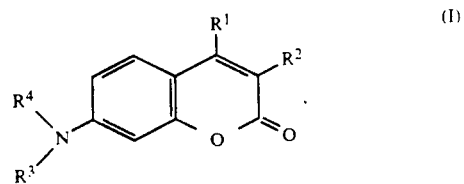

(I)

in which

R$^1$ denotes cyano,

R$^2$ represents phenyl or thiazolyl bonded in that 2-, 4- or 5-position, where phenyl is substituted by nitro, cyano, amino, —CH—C$_1$-C$_4$-alkyl, —C$_1$-C$_4$-alkyl-NH$_2$, —C$_1$-C$_4$-alkyl-NH—C$_1$-C$_4$-alkyl, carboxyl, C$_1$-C$_4$-alkoxycarbonyl, C$_1$-C$_4$-alkyl-carbonyloxy, hydroxyl, C$_1$-C$_4$-alkylamino-carbonyl or C$_1$-C$_4$-alkylcarbonylamino and can additionally be substituted by C$_1$l ∝ C$_4$-alkyl, fluorine, chlorine, or bromine, and where thiazolyl is monosubstituted or disubstituted by chlorine, cyano, where, in the case of disubstitution, the two substituents may be different and where the 4- and 5-position can together carry a fused benzene ring which can be substituted by carboxyl, amino or hydroxyl, R$^3$ denotes C$_1$-C$_4$-alkyl or C$_1$-C$_4$-alkoxycarbonyl-C$_1$-C$_4$-alkyl and R$^4$ represents C$_1$-C$_4$-alkyl which is substituted by hydroxyl, amino, carboxyl or C$_1$-C$_4$-alkoxy-carbonyl and provided that one of the radicals R$^2$, R$^3$ and R$^4$ carries a primary or secondary amino group, the hydroxyl group, the carboxyl group or the C$_1$-C$_4$-alkoxy-carbonyl group.

2. The coumarin derivative of claim 1 of the formula

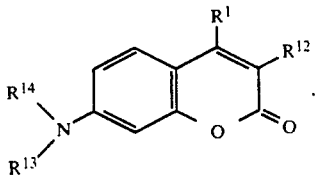

in which
- $R^1$ denotes cyano,
- $R^{12}$ represents phenyl or thiazolyl bonded in the 2-, 4 or 5-position, where phenyl can be substituted by carboxyl, $C_1$-$C_4$-alkyl-carbonyloxy, amino, —NH-$C_1$-$C_4$-alkyl, —$C_1C_4$-alkyl-NH$_2$, $C_1C_4$-alkyl, cyano, fluorine, chlorine or bromine and where thiazolyl can be substituted by chlorine, cyano or a benzene ring fused in the 4- and 5-position, which in turn can carry carboxyl or amino,
- $R^{13}$ denotes hydrogen, methyl or ethyl and
- $R^{14}$ represents —$C_1$—$C_4$-alkyl-OH, —$C_1$-alkyl-NH$_2$ or $C_1$-$C_4$-alkyl-COOH, where furthermore $R^{13}$ and $R^{14}$, together with the N atom which they substitute, can denote a morpholine ring, a piperazine ring or a triazolyl ring which can be substituted by methyl, phenyl or methyl and phenyl, and where furthermore one of the radicals $R^{12}$, $R^{13}$ and $R^{14}$ carries a primary or secondary amino group, the hydroxyl group, the carboxyl group or a $C_1$-$C_2$-alkoxycarbonyl group.

3. The coumarin derivative of claim 2 of the formula

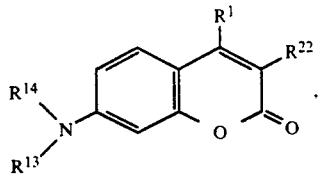

in which
- $R^1$, $R^{13}$ and $R^{14}$ assume the scope of meaning mentioned in claim 2 and
- $R^{22}$ represents phenyl or thiazolyl bonded in the 2-position, where phenyl can be substituted by para-carboxyl, para-amino, para-NH≧$C_1$-$C_4$-alkyl, para-CH$_2$-NH$_2$, cyano, methyl or ethyl and where thiazolyl can be substituted by chlorine, cyano or a benzene ring fused in the 4- and 5-position which in turn can carry carboxyl or amino, where furthermore one of the radicals $R^{13}$, $R^{14}$ and $R^{22}$ carries a primary or secondary amino group, the hydroxyl group or the carboxyl group.

* * * * *

UNITED STATES PATENT AND TRADEMARK OFFICE
CERTIFICATE OF CORRECTION

Page 1 of 2

PATENT NO. : 5,300,656
DATED : April 5, 1994
INVENTOR(S) : Eberhard Kuckert, et al.

It is certified that error appears in the above-identified patent and that said Letters Patent is hereby corrected as shown below:

| | |
|---|---|
| Column 20, line 43, | after "amino" cancel "-CH-$C_1$-$C_4$-alkyl," and substitute -- -NH-$C_1$-$C_4$-alkyl,-- |
| Column 20, line 48, | cancel "$C_1$I$\alpha C_4$-alkyl," and substitute --$C_1$-$C_4$-alkyl,-- |
| Column 21, line 13, | cancel "4or" and substitute --4- or-- |
| Column 21, line 15, | cancel "-$C_1 C_4$-alkyl-$NH_2$" and substitute — -$C_1$-$C_4$-alkyl-$NH_2$-- |

UNITED STATES PATENT AND TRADEMARK OFFICE
CERTIFICATE OF CORRECTION

PATENT NO. : 5,300,656
DATED : April 5, 1994
INVENTOR(S) : Eberhard Kuckert, et al.

It is certified that error appears in the above-identified patent and that said Letters Patent is hereby corrected as shown below:

Column 21, line 15, cancel "$C_1C_4$-alkyl" and substitute --$C_1$-$C_4$-alkyl--

Column 21, line 21, cancel "-$C_1$--alkyl-$NH_2$" and substitute --$C_1$-$C_4$--alkyl-$NH_2$--

Column 22, line 20, cancel "para-$NH \geq C_1$-$C_4$-alkyl" and substitute --para-$NH$-$C_1$-$C_4$-alkyl--

Signed and Sealed this

First Day of June, 1999

Attest:

Q. TODD DICKINSON

Attesting Officer

Acting Commissioner of Patents and Trademarks